United States Patent [19]
Rogalskyj et al.

[11] Patent Number: 5,925,317
[45] Date of Patent: Jul. 20, 1999

[54] DUAL NEUTRALIZATION SYSTEM FOR IODINE TREATMENT OF CONTACT LENSES

[75] Inventors: Jill S. Rogalskyj, Livonia; David J. Heiler, Avon; Alyce K. Dobie, Williamson, all of N.Y.

[73] Assignee: Bausch & Lomb Incorporated, Rochester, N.Y.

[21] Appl. No.: 08/760,915

[22] Filed: Dec. 6, 1996

Related U.S. Application Data

[60] Provisional application No. 60/010,402, Jan. 22, 1996.
[51] Int. Cl.$^6$ .............................. A61L 2/18; A01N 59/12
[52] U.S. Cl. .............................. 422/30; 422/37; 424/667; 424/672; 514/840
[58] Field of Search ........................ 422/30, 37; 424/667, 424/672; 514/840

[56] References Cited

U.S. PATENT DOCUMENTS

| | | | |
|---|---|---|---|
| 3,907,985 | 9/1975 | Rankin | 424/78 |
| 3,911,107 | 10/1975 | Krezanoski | 424/78 |
| 4,031,209 | 6/1977 | Krezanoski | 424/150 |
| 4,312,833 | 1/1982 | Clough et al. | 422/30 |
| 5,370,744 | 12/1994 | Chowhan et al. | 134/42 |
| 5,494,937 | 2/1996 | Asgharian et al. | 514/772.3 |

FOREIGN PATENT DOCUMENTS

| | | |
|---|---|---|
| 476777 | 9/1990 | European Pat. Off. . |
| 1472410 | 4/1997 | European Pat. Off. ........ A61L 13/00 |
| 96/00591 | 1/1996 | WIPO . |

OTHER PUBLICATIONS

L. Schutte and E. Havinga, "The Degradation Reaction of Histidine With Iodine," Recueil, vol. 86, pp. 385–392 (1967).

L. Schutte et al, "The Substitution Reaction of Histidine and Some Other Imidazole Derivatives Wiih Iodine," Tetrahedron, Supplement No. 7, pp. 295–306 (1966).

N.M. Alexander, "Reaction of Povidon–Iodine With Amino Acids and Other Important Biological Compounds," from Proceedings of the International Symposium on Povidone, University of Kentucky, College of Pharmacy, Apr. 17–20, 1983, Drs. G.A. Digenis and J. Ansell, eds.

*Primary Examiner*—Robert J. Warden
*Assistant Examiner*—E. Leigh McKane
*Attorney, Agent, or Firm*—Chris P. Konkol

[57] ABSTRACT

A method and system for disinfecting contact lenses with iodine using a neutralizing solution having a first, rapid neutralizing component which completes its reaction with available iodine in less than five seconds and a second, slower neutralizing component which completes its reaction with available iodine in about 3 to 30 minutes.

50 Claims, No Drawings

DUAL NEUTRALIZATION SYSTEM FOR IODINE TREATMENT OF CONTACT LENSES

This application claims the benefit of U.S. Provisional Application No. 60/010,402 filed on Jan. 22, 1996.

BACKGROUND OF THE INVENTION

1. Field of the Invention

This invention relates to the field of contact lens treatment, and more particularly relates to contact lens disinfection, and especially relates to the neutralization of iodine disinfectants used to treat contact lenses. In some aspects, this invention further relates to the simultaneous cleaning and disinfection of contact lenses using iodine as the active disinfectant.

2. Description of the Related Art

Iodine is a well-known disinfecting agent known to be useful against a variety of organisms, including viruses, bacteria, spores, yeast, molds, protozoa, fungi, worms, nematodes and the like. Because of the wide range of disinfecting capabilities, iodine has been suggested for use as a contact lens disinfectant. However, iodine is a strong irritant at higher concentrations and may, when used in concentration required for disinfection, destroy animal proteins and otherwise be harmful. Therefore, because of the potential harm to the eye, iodine is preferably neutralized before the disinfected lens is inserted in the eye.

Methods disclosing the neutralization of iodine as a contact lens disinfectant are known. See U.S. Pat. Nos. 3,911,107 and 4,031,209 to Krezanoski. Both patents disclose neutralizing the iodine in solution by slow dissipation methods and use compounds suitable for human and animal use. The neutralizing solution favored by Krezanoski contains sorbic acid and EDTA.

The Krezanoski patents also disclose compounds known as antioxidants that destroy available iodine. Examples of these compounds include alcohols, aldehydes, alkenes, alkynes, aromatic hydrocarbons, amides, quinones, hydroxy acids, sugars, amino acids, sulfites, thiosulfates, sulfhydryl containing compounds, and polyunsaturated organics. Solutions of such have been found to destroy all of the available iodine at different rates. Many such compounds will be satisfactory for various industrial purposes. However, safety and tissue tolerance requirements restrict the number of compounds suitable for human and animal use.

U.S. Pat. No. 4,312,833 to Clough issued Jan. 26, 1982, also teaches a method of disinfecting contact lenses using iodine. In Clough's process, contact lenses are contacted with a solution containing iodine and a reducing agent capable of reducing the available iodine level to substantially zero in a time of at least 30 minutes and at a temperature of from 20° to 25° C. The iodine is present as an iodophor and the preferred organic reducing agent is sodium formate.

Amino acids have been used to neutralize iodine. Histidine is not known to have been previously suggested for use in care regimens for contact lenses, although the oxidation reaction of histidine with an excess of iodine is discussed in a paper by Schutte, L., et al, "The Substitution Reaction of Histidine and Some Other Imidazole Derivatives With Iodine," Tetrahedron, Suppl. 7, pp. 295–306 (1965). One drawback to using an imidazole such as histidine is the formation of an oxidation product that decomposes to a brown degradation product.

Schutte, L., and Havinga, E., "The Degradation Reaction of Histidine With Iodine," Recueil 86: 385–392 (1967) further investigated the $I_2$-degradation of histidine. By-products included carbonate, iodoform, oxalic acid, ammonia and iodide products. Additionally, they studied the reactions of some imidazole derivatives: during the iodination of histamine, the initial formation of a brown precipitate, probably a diiodo product, was observed. This dissolved in the further course of reaction. It was also suggested that histidine methyl ester follows a different reaction path as no iodoform is formed during its degradation as with the oxidation of histidine and histamine.

Alexander, N. M., "Reaction of Povidone-Iodine With Amino Acids and Other Important Biological Compounds," Proceeding of the International Symposium on Povidone, pp. 274–288 (University of Kentucky College of Pharmacy, Lexington, Ky., 1983) reports studies of the reaction of povidone-iodine with amino acids, peptides and other biological molecules. Methionine, histidine, cysteine, tyrosine and tryptophan reacted with povidone-iodine, whereas all of the other common amino acids (such as alanine, arginine, aspartic acid, cystine, glutamic acid, glycine, isoleucine, leucine, lysine, phenylalanine, proline, serine, threonine, and valine), did not react.

In addition to disinfection, the contact lens should also be cleaned of any debris. This debris is in the form of lipids, mucins and proteins that accumulates as a result of normal contact lens wear. Surfactants may remove the looser bound debris but an enzyme, or a combination of enzyme and surfactants, may be needed to remove protein which is harder to remove. Cleaning and disinfection may involve two separate steps with the cleaning occurring first but may be performed simultaneously with certain disinfectants and enzymes. Single step systems have a substantially greater compliance rate.

Another common compliance issue deals with the rubbing that typically accompanies cleaning and the rinsing that is often required to remove any residual cleaner or debris from the lens. A single step cleaning and disinfecting system with no rubbing or rinsing is the goal of many contact lens solution companies but currently, no solution succeeds in meeting all these requirements.

There are many products on the market that remove surface debris from a contact lens. Daily cleaners usually contain surfactants. Weekly cleaners usually contain proteolytic enzymes. Both types of products usually require the lenses to be rubbed and rinsed after use. With a daily cleaner, the rub and rinse occurs prior to disinfection while with the enzymatic cleaner, a rinse to remove any lens debris may occur prior to insertion of the lens into the eye.

An example of cleaning methodology requiring rubbing is provided in U.S. Pat. No. 3,907,985 to Rankin issued Sep. 23, 1975. This reference discloses an ophthalmic solution comprising an aqueous solution of polystyrene sulfonate having a molecular weight between 75,000 to 10,000,000, and preferably polyethylene glycol. The solution as disclosed provides a lubricant and cushioning effect to traumatized eyes along with providing a cleaning function. The cleaning method disclosed comprises the steps of soaking a lens in the ophthalmic solution followed by rubbing the lens between the fingers and subsequently rinsing the lens with water. Although the reference stated that the disclosed regimen cleaned debris from lenses, there was no specific description of protein removal.

Iodine is a highly effective contact lens disinfectant from the perspective of antimicrobial efficacy but iodine disinfectant systems have a tendency to discolor lenses. Performance of systems such as those disclosed by Krezanoski is difficult to control because neutralization is highly dependent on ambient light conditions. Moreover, sorbic acid can be irritating and sorbic acid solutions may have an undesirable color.

Current regimens for the care of nondisposable, soft contact lenses typically require several component products: a daily cleaner, a weekly cleaner, and a disinfectant. Regimens combining weekly cleaning and disinfecting are known, but more effective and convenient care regimens have long been sought.

SUMMARY OF THE INVENTION

It has now been discovered that it is possible to employ a safe contact lens cleaning and disinfection system utilizing iodine and a dual neutralization system that insures complete neutralization of the iodine with virtually no discolored lenses. With a thorough rinse at the end of the regimen, there is no need to soak the contact lens for extended periods of time to complete iodine neutralization. It has also been discovered that the disinfection system of this invention may be desirably combined with sulfonate polymer to clean and disinfect in one fast, convenient step, eliminating the need for a separate weekly cleaner.

The disinfecting system of this invention contains an iodophor and a neutralizing solution which contains two neutralizers. One neutralizer acts almost instantaneously (reaction between the neutralizer and available iodine will be completed in less than about 5 seconds, preferably less than a second). The second neutralizer acts slower, over a period of minutes. The amount of iodine provided in the system is such that active iodine will be at a disinfecting level after the iodophor and rapid neutralizer react. The second, slower neutralizer gradually neutralizes iodine at a rate that allows contact lens disinfection to occur. Iodine disinfection occurs in a matter of minutes. An important aspect of the disinfecting system of this invention is the rinse that occurs after disinfection is complete. Inclusion of the rapid neutralizer in a neutralizing solution neutralizes residual iodine on the lens during the rinse. The rinsed lenses are safe to be inserted into the eyes and worn.

The disinfecting and cleaning system of this invention includes the disinfecting system described above and additionally includes a cleaner. Selection of the cleaning component is not narrowly critical. A presently preferred cleaner is a sulfonate polymer, particularly polystyrene sulfonate. The cleaner is preferably such that the cleaning is accomplished simultaneously with the disinfecting. Still more preferably, the cleaner is capable of removing debris from the contact lens without rubbing. In the more preferred aspects of this invention, separate weekly cleaning is not necessary for the care of contact lenses.

In one embodiment of this invention, the disinfectant, iodine, is preferably provided as a tablet. The amount of active iodine provided is such that a disinfecting amount remains after the initial rapid neutralization. Sulfonate cleaners, if used, are preferably included in the tablet. However, other cleaners may be included in either the tablet or in the neutralizing solution, as will be apparent to one of ordinary skill in the art.

In another embodiment of this invention, iodine is provided as a stabilized solution. A problem with using stabilized iodine solutions as a contact lens disinfectant is that the iodine concentrations of such solutions are very high compared to the concentrations required to disinfect contact lenses. For example, stabilized iodine solutions for ophthalmic use contain from about 100 to 1000 ppm iodine and typically contain about 300 ppm iodine. Instability of iodine solutions increases as concentrations are reduced below these levels. Contact lens disinfection, however, requires only about 50 ppm iodine. The vast excess of iodine in stabilized solutions increases the incidence of lens discoloration and iodine retention in the lens. When using the disinfection system of this invention with a stabilized iodine solution, the amount of rapid neutralizer is selected to reduce the available iodine in stabilized solutions to levels required for contact lens disinfection and the amount of the slower neutralizer is selected to complete neutralization in a time that allows for lens disinfection. In this embodiment, the neutralizers may be provided in tablet form, although a solution is still preferred.

The present lens cleaning and disinfecting preferably takes place in a single step. It is easy to use with a short amount of time required. The lenses are disinfected and effective cleaning occurs every time the lenses are cycled through the regimen. This results in lenses that are more comfortable, with less eye irritation.

DETAILED DESCRIPTION OF THE INVENTION

The disinfecting system of this invention comprises three components: an iodine component and two neutralizing components. The iodine component is preferably provided separate from the two neutralizing components. In the embodiment of this invention where the neutralizing components are used to rinse residual iodine from contact lenses, the neutralizing components will preferably be provided as a solution and the iodine component will preferably be provided as a tablet. However, in another preferred embodiment of this invention, the iodine component is provided as a stabilized solution and the neutralizing components are provided in tablet or powder forms or as a solution, preferably as a solution. Stabilized iodine solutions are well known in the art and will not be further described here. See, for example, European Patent Publication Number 476,777 by Dagra Pharma B. V., entitled "An Ophthalmic Preparation Comprising a Povidone-Iodine Solution."

Iodine is preferably provided as an iodophor. Any iodophor that provides active iodine upon solution is suitable for use in the present invention. Iodophors are commercially available and will provide a known amount of active iodine from the iodophor complex upon dissolving in aqueous solution. It is believed that the active iodine is responsible for the disinfection properties noted in the solutions of the present invention. The iodine associated with the iodophor complex and the active iodine free in the solution are collectively referred to as the total available iodine in the system.

Particularly useful carriers that associate with iodine to create iodophors include a variety of high molecular weight polymeric materials such as starch and various synthetic polymers. Preferred synthetic polymers are polyvinyl pyrrolidone and copolymers of polyvinyl pyrrolidone such as vinyl acetate polyvinyl pyrrolidone, polyvinyl oxazolidone, caprolactam, polyvinyl alcohols, amides and phenols. Specific examples of iodophors useful in this invention include polyvinylpyrrolidone-iodine, polyvinyl alcohol-iodine, polyvinyl oxazolidone-iodine, polyvinyl imidazole-iodine, polyvinyl morpholone-iodine, polyvinyl caprolactam-iodine, nonylphenolethoxylate-iodine, soluble starch-iodine, betacyclodextrin-iodine, polyoxyethylenepolyoxypropylene condensate-iodine, and ethoxylated linear alcohol-iodine, with polyvinyl pyrrolidone-iodine being the most preferred. An added benefit of using polyvinyl pyrrolidone-iodine in the disinfection system is that the polyvinyl pyrrolidone remaining after dissolution and neutralization of the iodophor serves as a wetting agent for the contact lens.

The iodophor may be provided as a solid or liquid to the disinfection system of the present invention. However, the iodophor is most conveniently provided in a solid form (e.g., tablet or powder, etc.). The amount of iodophor required to yield a desired amount of active iodine will vary slightly among different iodophors. USP grade polyvinyl pyrrolidone-iodine (PVP-$I_2$) contains about 9% to about 12% total available iodine.

The amount of iodophor required can be easily determined by one of ordinary skill in the art. Iodine is preferably provided in tablets which, upon dissolution and after reaction with the rapid neutralizer, produce a disinfecting amount of iodine. A disinfecting amount is that amount necessary to disinfect contact lenses. Selection of a disinfecting amount is within the skill of the art. Preferably, the concentration of active iodine in solution after reaction with the rapid neutralizer is within the range from about 20 to about 80 ppm, preferably 30–70 ppm, more preferably 40 to 60 ppm. Iodine is preferably provided in amounts which, upon dissolution and before reaction with the rapid neutralizer, produce concentrations of active iodine in solution within the range from about 30 to about 1000 ppm, preferably 40–500 ppm, more preferably 40–100 ppm.

The first of the two neutralizing components of the disinfecting system of this invention completes its reaction with available iodine almost instantaneously—preferably the reaction is complete in less than five seconds, more preferably less than one second. Selection of a suitable neutralizer is generally within the skill of the art. Preferred rapid neutralizers include inorganic sulfites and thiosulfates, methionine, cysteine, and ascorbic acid. Inorganic thiosulfates, especially sodium thiosulfate, are particularly preferred rapid neutralizers. The amount of rapid neutralizer employed will generally be such that a disinfecting amount of iodine remains after mixing the neutralizing component and the iodine component of the system. Thus, in the embodiment of this invention where the disinfected lens is rinsed with neutralizing solution, the "excess" iodine is directly related to the rapid neutralizer concentration in the rinse solution. When the iodine component is provided as a tablet and the neutralizing components are provided as a solution which is to be used as a rinse, the amount of rapid neutralizer in the solution is preferably within the range of about 50–100 ppm, more preferably about 60–80 ppm.

The second of the two neutralizing components of the disinfecting system of this invention gradually neutralizes iodine at a rate that allows contact lens disinfection to occur. The reaction between the second neutralizing component and available iodine is preferably complete in about 3 to about 30 minutes, more preferably about 5–10 minutes. Selection of a suitable neutralizer is generally within the skill of the art. Preferred slower neutralizers include imidazoles, mixtures of sorbic acid and EDTA (ethylene diamine tetraacetic acid), and sodium formate. Imidazoles are particularly preferred, especially histidine and histidine derivatives. The amount of slower neutralizer employed will generally be sufficient to neutralize the disinfecting amount of iodine remaining after mixing the neutralizing component and the iodine component of the system. The amount of slower neutralizer is generally related to the disinfecting amount of iodine which is selected as described above, to the desired time of the disinfecting/neutralizing cycle, and to the pH of the system. The reaction time of the slower neutralizer is surprisingly dependent on system pH. The pH of the solution formed by mixing the iodine and neutralizing components is preferably in the range of about 6 to about 8, more preferably about 6.8 to about 7.6. When the iodine component is provided as a tablet and the neutralizing components are provided as a solution which is to be used as a rinse, the amount of slower neutralizer in the solution is preferably within the range of about 100–2000 ppm, more preferably about 500–1500 ppm.

As mentioned, imidazoles are preferred slower neutralizers. The weakly basic imidazole ring neutralizes iodine at a rate that allows for contact lens disinfection. Histidine is a particularly preferred imidazole since it is a naturally-occurring amino acid. However, side reactions with some imidazoles can produce precipitates and colored solutions. For example, colored byproducts may be formed upon further decomposition of the iodinated ring. See Schutte, L., and Havinga, E., "The Degradation Reaction of Histidine With Iodine," *Recueil*, Vol. 86, pp. 385–392 (1967). Without wishing to be bound by any theory of operability, it is believed that this problem can be overcome by tying up the electrons of the amino group to prevent attack on the iodinated imidazole ring, dissipating the overall charge of the amino nitrogen. Substitution of an electron-withdrawing group on the amino nitrogen will generally be effective. Examples of suitable electron-withdrawing groups include amides, imides, phenyls, substituted phenyls, perfluoro alkyls, and sulfonamides. A preferred solution to this problem is to use N-alpha-acetyl histidine as the slower neutralizer. When an acetyl group is attached to the amino nitrogen of histidine, attack on the imidazole ring is blocked.

N-alpha-acetyl histidine neutralizes active iodine over a period of minutes, leaving minimal time for iodine to migrate into the lens matrix. A faint yellow color may be present on the surfaces of some lenses. However, the color can be easily rinsed off or neutralized by rinsing the lenses with a solution containing the fast neutralizer of this invention.

Other components used in conventional contact lens care regimens may be combined with the disinfecting system of this invention. For example, a cleaner may be combined with the disinfecting system to simultaneously clean and disinfect lenses. The selection of the cleaner is not narrowly critical. Some conventional contact lens cleaners such as poloxamine are not suitable because they are incompatible with iodine. As a further example, the neutralizers are preferably provided as a solution and the solution will be preserved. Selection of suitable preservatives is well within the skill of the art. A presently preferred preservative is polyhexamethlylene biguanide. Other components include chelating agents, tonicity adjusting agents, and buffers. The preferred neutralization component is substantially iso-osmotic and has a substantially neutral pH.

An iodine chromophore may be added to the disinfecting system to allow iodine neutralization to be seen visually. This has the benefit of encouraging compliance with the lens care regimen and discouraging consumers from putting active iodine in their eyes. The chromophore is preferably incorporated into the iodophor-containing tablet. The indicator provides a color to the disinfecting solution, indicating the continued presence of oxidative disinfectants. The iodine chromophore may be any color producing complex comprising iodine or iodine derivative ions associated with an amylose-containing compound or complex. "Chromophore" refers to any color-producing compound. An amylose is the linear, helical component of starch. Preferred amylose-containing compositions are starch and hydrolyzed starches such as dextrins, with maltodextrin being particularly preferred.

When the iodophor-containing tablet initially contacts the neutralizing solution, the indicator will turn the solution purple. The rapid neutralizing agent will reduce the amount of iodine but the solution will retain the purple hue. It is the second, slower acting neutralizer that will cause the solution to turn clear, indicating the neutralization of the iodine in solution.

In one embodiment of this invention, iodine is preferably provided as a tablet. Tablet preparation is done using techniques well known in the art.

This invention will be further illustrated by reference to the following Examples.

EXAMPLE 1

Preparation of Neutralizing Solution with Two Neutralizers

EXAMPLE 1

|  | weight (gm) | percent % |
| --- | --- | --- |
| Boric Acid | 50.0 | 1.25 |
| Sodium Borate | 14.0 | 0.35 |
| Disodium EDTA | 0.4 | 0.01 |
| Sodium Chloride | 12.4 | 0.29 |
| Tetronic ® 1107 (BASF) | 0.2 | 0.005 |
| Sodium Thiosulfate, pentahydrate | 0.28 | 0.007 |
| N-alpha-Acetyl-L-histidine | 3.6 gm | 0.09 |

Pipette into the solution 2.37 mL of 1350.8 ppm stock solution of polyaminopropyl biguanide (PHMB HCL 20% solution, from ICI Americas as Cosmocil CQ). The final solution was brought up to a volume of 4000 gm with purified water before the pH and osmolality was recorded. The pH of this solution was 7.4 and the osmolality was 320.

EXAMPLE 2

Preparation of Rapid Disinfecting Tablet (90 ppm Active Iodine)

An iodine disinfecting tablet designed to be dissolved in 10 mLs of reducing solution was prepared having the following formulation:

7.5 mg PEG-8000, 325 mesh particle size 8.2 mg PVP-Iodine, micronized 12.0 mg Maltrin® M040 (Grain Processing Corp.)

65.0 mg lactose anhydrous 10.0 mg sodium polystyrene sulfonate, micronized 14.0 mg citric acid, anhydrous 32.8 mg sodium bicarbonate 7.5 mg sodium benzoate, 80 mesh Prior to compounding, the Maltrin M040 was milled and passed through a #200 mesh sieve. Sodium benzoate was also milled and passed through a #80 mesh sieve. Lactose, citric acid and the maltrin were dried at 65–75 degree C. The PEG, PVP-Iodine, polystyrene sulfonate and maltrin were then hand mixed and passed through a #50 mesh sieve. The citric acid, sodium bicarbonate and part of the lactose were separately mixed for 20 minutes. This mixture was then combined with the PVP-Iodine mixture and the remaining lactose added. After mixing for 30 minutes in a V-Blender, the sodium benzoate is added for an additional mixing period of 5 minutes. Tableting was done with a 7 mm punch for a tablet weight of 157.0 mg.

EXAMPLE 3

Disinfecting Activity

The antimicrobial activity of the iodophor and neutralizer solution was tested by exposing the test organism at about $1.0 \times 10^7$ to about $1.0 \times 10^8$ colony forming units per milliliter (CFU/mL) to 10 mL of each composition at room temperature for the intervals of 1, 2.5 or 5 minutes (the solution was swirled at approximately 3 minutes). An aliquot of each inoculated sample was removed at the measured time, diluted in a neutralizing both (Dey-Engley) and plated with neutralizing agar. The agar plates were incubated for 2 to 5 days and plate counts were determined to calculate reduction in CFU/mL for each organism.

A disinfecting solution made from the tablet and neutralizing solution previously described was tested in duplicate against the following organisms *S. aureus* ATCC 6538P, *P. aeruginosa* ATCC 9027, *S. marcescens* ATCC 13880, *C. albicans* ATCC 10231, and *F. solani* ATCC 36031. Log reduction values are shown in Table 1.

TABLE 1

|  | 1 minute | 2.5 minutes | 5 minutes |
| --- | --- | --- | --- |
| *S. aureus* | 0.3 | >4.3 | >4.3 |
| *S. aureus* | 0.1 | >4.3 | >4.3 |
| *P. aeruginosa* | 1.1 | >4.4 | >4.4 |
| *P. aeruginosa* | 1.0 | >4.4 | >4.4 |
| *S. marcescens* | 0.0 | 3.0 | >4.2 |
| *S. marcescens* | 0.1 | >4.2 | >4.2 |
| *C. albicans* | 0.0 | 2.2 | 3.4 |
| *C. albicans* | 0.0 | 2.0 | 3.8 |
| *F. solani* | 0.0 | >3.9 | >3.9 |
| *F. solani* | 0.0 | 3.7 | >3.9 |

For disinfecting contact lenses, the International Standards Organization requires a greater than 3 log reduction for bacteria (ISO/CEN4). The iodophor and neutralizer solution satisfied the ISO criteria for both trials at the 2.5 minute time point when tested with *S. aureus* and *P. aeruginosa* and met the requirements for at least one of the two trials of *S. marcescens*. At the 2.5 minute time point, the solution met ISO criteria for yeast and mold (greater than 1 log reduction) against *C. albicans* and *F. solani* at the 2.5 minute time point for both trials.

At the 5 minute time point all organisms tested met the ISO criteria for a contact lens disinfecting solution.

EXAMPLE 4

Comparison of Currently Marketed Lenses

In this Example, currently marketed lenses were subjected to the disinfection regimen to identify which lenses needed a post disinfection rinse with the neutralizing solution. The lenses were subjected to the following regimen:

1. Place lenses in basket of 10 mL lens case.

2. Place 1 disinfecting tablet (from Example 2), 10 mL of neutralizer (from Example 1) and the lens basket containing the lens into the lens case.

3. After approximately 3 minutes, swirl the case gently. The solution should be purple.

4. Let lenses stand for a total of 10 minutes.

5. Remove the lenses from the case. Lenses may be ready to wear. If yellow color is present on lens surface, further handling may be necessary (see Table 2).

TABLE 2

| LENS TRADE NAME | MATERIAL | ACTION |
|---|---|---|
| Acuvue ® (Johnson & Johnson) | etafilcon A | Remove from system No further handling |
| Surevue ® (Johnson & Johnson) | etafilcon A | Remove from system No further handling |
| Newvue ® (Ciba Vision) | vivfilcon A | Remove from system No further handling |
| Optima FW ® Visibility (Bausch & Lomb) | polymacon | Remove from system No further handling |
| Medalist ® (Bausch & Lomb) | polymacon | Remove from system 10 sec/side rinse |
| Focus ® (Ciba Vision) | vivfilcon A | Remove from system No further handling |
| Cibasoft ® (Ciba Vision) | tefilcon | Remove from system 10 sec/side rinse |
| Optima ® Toric (Bausch & Lomb) | hefilcon B | Remove from system 10 sec/side rinse |
| SeeQuence II ® (Bausch & Lomb) | polymacon | Remove from system 10 sec/side rinse |
| CSI Clarity Clear ® (Pilkington) | crofilcon A | Remove from system 10 sec/side rinse |

We claim:

1. In a method for treating a contact lens which comprises disinfecting the lens with a disinfecting amount of iodine, the improvement of which comprises:
   (a) providing a neutralizing solution comprising a first, rapid neutralizing component that completes its reaction with available iodine in less than five seconds and a second, slower neutralizing component that completes its reaction with available iodine in about 3 to 30 minutes;
   (b) forming a solution by combining the neutralizing solution and iodine, the amount of iodine provided such that a disinfecting amount remains after the iodine and the first, rapid neutralizing component react;
   (c) contacting the lens with the solution for a sufficient time to disinfect the lens and neutralize the iodine in the solution; and
   (d) rinsing the lens.

2. The method of claim 1 wherein the iodine is in the form of an iodophor.

3. The method of claim 2 wherein the iodophor is selected from the group consisting of polyvinylpyrrolidone-iodine, polyvinyl alcohol-iodine, polyvinyl oxazolidone-iodine, polyvinyl imidazole-iodine, polyvinyl morpholone-iodine, and polyvinyl caprolactam-iodine, nonylphenolethoxylate-iodine, soluble starch-iodine, betacyclodextrin-iodine, polyoxyethylenepolyoxypropylene condensate-iodine, ethoxylated linear alcohol-iodine, and mixtures thereof.

4. The method of claim 2 wherein the iodine is in the form of polyvinyl pyrrolidone-iodine.

5. The method of claim 2 wherein the iodophor is provided in a solid form.

6. The method of claim 5 wherein neutralizing solution contains about 50 to 100 ppm of the first neutralizing component.

7. The method of claim 6 wherein neutralizing solution contains about 60 to 80 ppm of the first neutralizing component.

8. The method of claim 5 wherein the iodophor-containing solid further comprises an iodine chromophore.

9. The method of claim 1 wherein the amount of active iodine in solution after reaction of the iodine and the first neutralizing component is within the range from about 20 to about 80 ppm.

10. The method of claim 9 wherein the amount of active iodine in solution after reaction of the iodine and the first neutralizing component is within the range from about 30 to about 70 ppm.

11. The method of claim 10 wherein the amount of active iodine in solution after reaction of the iodine and the first neutralizing component is within the range from about 40 to about 60 ppm.

12. The method of claim 1 wherein the first neutralizing component completes its reaction with available iodine in less than one second.

13. The method of claim 1 wherein the first neutralizing component is selected from the group consisting of inorganic sulfites and thiosulfates, methionine, cysteine, ascorbic acid, and mixtures thereof.

14. The method of claim 13 wherein the first neutralizing component is selected from the group consisting of inorganic thiosulfates.

15. The method of claim 14 wherein the first neutralizing component is sodium thiosulfate.

16. The method of claim 1 wherein the second neutralizing component completes its reaction with available iodine in about 5 to 10 minutes.

17. The method of claim 1 wherein the second neutralizing component is selected from the group consisting of imidazoles, mixtures of sorbic acid and EDTA, sodium formate, and mixtures thereof.

18. The method of claim 17 wherein the second neutralizing component is selected from the group consisting of imidazoles.

19. The method of claim 18 wherein the second neutralizing component is selected from the group consisting of histidine and histidine derivatives having an electron withdrawing group on the amino nitrogen.

20. The method of claim 19 wherein the lens is rinsed with said neutralizing solution.

21. The method of claim 20 wherein the electron withdrawing group is selected from the group consisting of amides, imides, phenyls, substituted phenyls, perfluoro alkyls, and sulfonamides.

22. The method of claim 21 wherein the second neutralizing component is N-alpha-acetyl histidine.

23. The method of claim 1 wherein the pH of the solution formed in step (b) is within the range of about 6 to 8.

24. The method of claim 23 wherein the pH of the solution formed in step (b) is within the range of about 6.8 to 7.6.

25. The method of claim 1 wherein the solution formed in step (b) further comprises a cleaner.

26. The method of claim 1 wherein the neutralization solution further comprises a preservative.

27. A system for disinfecting contact lenses comprising:
   (a) a neutralizing solution comprising a first, rapid neutralizing component capable of completing its reaction with available iodine in less than five seconds and a second, slower neutralizing component capable of completing its reaction with available iodine in about 3 to 30 minutes and
   (b) iodine.

28. The system of claim 27 wherein the iodine is in the form of an iodophor.

29. The system of claim 28 wherein the iodophor is selected from the group consisting of polyvinylpyrrolidone-iodine, polyvinyl alcohol-iodine, polyvinyl oxazolidone-iodine, polyvinyl imidazole-iodine, polyvinyl morpholone-iodine, and polyvinyl caprolactam-iodine, nonylphenolethoxylate-iodine, soluble starch-iodine, betacyclodextrin-iodine, polyoxyethylenepolyoxypropylene condensate-iodine, ethoxylated linear alcohol-iodine, and mixtures thereof.

30. The system of claim 28 wherein the iodine is in the form of polyvinyl pyrrolidone-iodine.

31. The system of claim 28 wherein the iodophor is provided in a solid form.

32. The system of claim 31 wherein neutralizing solution contains about 50 to 100 ppm of the first neutralizing component.

33. The system of claim 32 wherein neutralizing solution contains about 60 to 80 ppm of the first neutralizing component.

34. The system of claim 31 wherein the iodophor-containing solid further comprises an iodine chromophore.

35. The system of claim 27 wherein the first neutralizing component is capable of completing its reaction with available iodine in less than one second.

36. The system of claim 27 wherein the first neutralizing component is selected from the group consisting of inorganic sulfites and thiosulfates, methionine, cysteine, ascorbic acid, and mixtures thereof.

37. The system of claim 36 wherein the first neutralizing component is selected from the group consisting of inorganic thiosulfates.

38. The system of claim 37 wherein the first neutralizing component is sodium thiosulfate.

39. The system of claim 27 wherein the second neutralizing component is capable of completing its reaction with available iodine in about 5 to 10 minutes.

40. The system of claim 27 wherein the second neutralizing component is selected from the group consisting of imidazoles, mixtures of sorbic acid and EDTA, sodium formate, and mixtures thereof.

41. The system of claim 40 wherein the second neutralizing component is selected from the group consisting of imidazoles.

42. The system of claim 41 wherein the second neutralizing component is selected from the group consisting of histidine and histidine derivatives having an electron withdrawing group on the amino nitrogen.

43. The system of claim 42 wherein the electron withdrawing group is selected from the group consisting of amides, imides, phenyls, substituted phenyls, perfluoro alkyls, and sulfonamides.

44. The system of claim 43 wherein the second neutralizing component is N-alpha-acetyl histidine.

45. The system of claim 27 wherein the neutralization solution further comprises a preservative.

46. The system of claim 27 wherein the system further comprises a contact lens cleaner.

47. The system of claim 46 wherein the neutralizing system further comprises a contact lens cleaner.

48. The system of claim 46 wherein the iodine is provided as a tablet.

49. The system of claim 48 wherein the cleaner comprises a sulfonate polymer.

50. The system of claim 49 wherein the cleaner comprises polystyrene sulfonate.

* * * * *